United States Patent [19]

Scymanski et al.

[11] Patent Number: 4,716,251
[45] Date of Patent: Dec. 29, 1987

[54] DIARYLOXYALKANE BROMINATION PROCESS

[75] Inventors: Gerald L. Scymanski, Trenton; Amgad S. Mossaad, South River; Saadat Hussain, East Brunswick, all of N.J.

[73] Assignee: Ethyl Corporation, Richmond, Va.

[21] Appl. No.: 826,994

[22] Filed: Feb. 7, 1986

[51] Int. Cl.$^4$ .................. C07C 41/18; C07C 43/225
[52] U.S. Cl. .................. 568/645; 568/637; 568/639
[58] Field of Search .................. 568/645, 637, 639

[56] References Cited

U.S. PATENT DOCUMENTS 3,752,856  8/1973  Nagy et al. .................. 568/639
3,833,674  9/1974  Brackenridge .................. 568/639 X
4,223,169  9/1980  Barda .................. 568/645

OTHER PUBLICATIONS

Raiford et al., Jour. Amer. Chem. Soc., vol. 51, (1929), 1776–1778.

Primary Examiner—Werren B. Lone
Attorney, Agent, or Firm—Donald L. Johnson; John F. Sieberth; W. G. Montgomery

[57] ABSTRACT

Diaryloxyalkanes such as diphenoxyethane are brominated to give a product containing an average of about 5–7 bromine atoms per molecule by commingling a solution of the diaryloxyalkane in a haloalkane solvent with an excess of liquid bromine in the absence of a bromination catalyst.

19 Claims, No Drawings

DIARYLOXYALKANE BROMINATION PROCESS

BACKGROUND OF THE INVENTION

Brominated diphenoxyethane is a commercial fire retardant. In its commercial form it is mainly either 1,2-bis(2,4,6-tribromophenoxy)ethane or 1,2-bis(pentabromophenoxy)ethane. In the prior art these compounds have been made by the reaction of a brominated phenol (e.g. 2,4,6-tribromophenol) with a halogenated alkane (e.g. 1,2-dichloroethane) at an elevated temperature in the presence of a base (e.g. potassium hydroxide) Anderson U.S. Pat. No. 3,833,538.

Methods of brominating other aromatic compounds have been described in the prior art. Typical procedures are set forth in Stepniczka U.S. Pat. Nos. 3,965,197; Garman et al. 4,287,373; Ayres 4,327,227; Nagy et al. 3,752,856; Britton et al. 2,022,634: and Bzaokenridge 3,833,674.

SUMMARY OF THE INVENTION

According to the present invention, a process for brominating diaryloxyalkanes has been discovered that gives a narrow product range, high yield and good color. The new process comprises mixing a solution of a diaryloxyalkane in an inert haloalkane solvent with liquid bromine. When the desired product is a hexabromodiaryloxyalkane, the use of a bromination catalyst is unnecessary and can be deleterious.

DESCRIPTION OF THE PREFERRED EMBODIMENTS

A preferred embodiment of the invention is a process for brominating a diaryloxyalkane, said process comprising:

(a) commingling a solution of said diaryloxyalkane in a haloalkane solvent with liquid bromine at a temperature from about 0° C. up to the reflux temperature of the mixture;

(b) allowing the resultant mixture to react to form the desired brominated diaryloxyethane; and (c) recovering said brominated diaryloxyalkane.

The process can be carried out using a broad range of diaryloxyalkanes as long as they have an unsubstituted position on a benzene ring capable of bromination. Some examples of suitable starting materials are:

1,2-di(4-ethylphenoxy)ethane,
1,3-diphenoxypropane,
2,2-diphenoxypropane,
1,4-diphenoxybutane,
1,6-diphenoxyhexane,
1,2-di(4-chlorophenoxy)ethane,
1,2-di(2-bromophenoxy)ethane,
1,2-di(2,4-dibromophenoxy)ethane,
1,(2,4-dibromophenoxy)-2-phenoxy ethane,
1,2-di(4-phenylphenoxy)ethane,
1,2-(4-phenoxyphenoxy)ethane,
1,2-di($\alpha$-naphthoxy)ethane, and the like.

The more preferred starting materials are the 1,2-diaryloxyethanes and especially 1,2-diphenoxyethane.

The amount of bromine should be an amount in stoichiometric excess of the amount required to insert the desired number of bromine atoms. For example, if hexabromodiphenoxyethane is the desired product, the amount of bromine should be in excess of 6 moles per mole of diphenoxyethane. If the desired product is decabromodiphenoxyethane, the amount of bromine should be in excess of 10 moles per mole of diphenoxyethane. Preferably the amount of bromine should be at least 75% in excess of the stoichiometric amount. More preferably, the bromine should be at least 100% in excess of the stoichiometric amount. Still more preferably the bromine should be used in excess of 150% of the stoichiometric amount. Best results were obtained in making 1,2-di(tribromophenoxy)ethane when using about a 200% stoichiometric excess of bromine (18 moles bromine per mole diphenoxyethane). There is no real upper limit except for economic reasons. Hence there is no benefit in exceeding about 400% stoichiometric excess.

Unless a high degree of bromination is desired, the process is conducted without the addition of a strong Lewis Acid bromination catalyst such as aluminum chloride, aluminum bromide, ferric chloride, ferric bromide, aluminum metal, iron metal and the like. In practice up to about 3 bromine atoms per benzene ring can be readily introduced without the use of a catalyst. After the initial reaction to introduce a portion of the desired bromine atoms, the reaction can be continued to obtain further bromination by adding a bromination catalyst. When this is done, perbromination can be obtained. The amount of catalyst added in the second step to achieve perbromination should be a catalytically effective amount. A useful range is about 0.001–0.5 weight percent based on the bromine charge. A more useful range is about 0.1–0.3 weight percent.

The diaryloxyalkane is dissolved in a haloalkane solvent. This solution may be prepared in advance or the solvent and diaryloxyalkane can be co-fed or mixed in line upon addition to the bromine.

Suitable solvents include any of the inert haloalkanes such as methylene chloride, 1,2-dichloroethane, 1,1,2-trichloroethane, 1,1,1-trichloroethane, sym-tetrachloroethane, 2,2-dichloropropane, carbon tetrachloride, chloroform, 1,2-dichlorobutane as well as the bromine analogs of the foregoing. The preferred solvent is methylene chloride, $CH_2Cl_2$.

The amount of solvent should be a solvent amount, that is, an amount that can dissolve the diaryloxyalkane at a reasonable temperature below reflux. A useful amount is about 1–20 parts by weight solvent for each part of diaryloxyalkane. More preferably, the amount of solvent is about 2–5 parts per part of diaryloxyalkane.

The bromine can be added to the diaryloxyalkane solution or the diaryloxyalkane solution can be added to the bromine or both reactants can be concurrently fed to a reaction zone. More preferably the diaryloxyalkane solution is added to the liquid bromine.

The reaction can be carried out over a broad temperature range. A useful range is from about 0° C. up to the boiling point of the solvent. Preferably, the reaction is started at a low temperature, e.g. about 10°–35° C. and more preferably ambient, and permitted to warm up as the reaction proceeds by the heat evolved in the reaction. The reaction can be completed without application of heat at temperatures below reflux. In order to reduce the reaction time it is beneficial to apply heat towards the end of the reaction to raise the temperature to reflux which is about 46° in the case of methylene chloride.

After the reaction is complete the product can be recovered by mixing the reaction mass with water and distilling out the solvent and any unreacted bromine. The solvent and bromine can be dried and recycled. The product remains as an aqueous slurry. A small amount of aqueous caustic can be added to remove any residual elemental bromine. The product is then recovered from the aqueous slurry by filtration or centrifugation and then dried and ground to the desired particle size.

The following examples will serve to illustrate how to conduct the process.

EXAMPLE 1

In a reaction vessel was placed 287.6 grams (1.8 moles) of bromine. While stirring, a solution of 21.4 (0.1 mole) of 1,2-diphenoxyethane in 30 mls of 1,2-dichloroethane was added at 20°-25° C. over a period of 65 minutes. The reaction mixture was stirred for 18 hours at ambient temperature. About 100 mls of water were then added to quench the reaction mixture. The unreacted bromine and solvent were then distilled from the mixture under vacuum and the product was recovered by filtration. Product recovery indicated a 100% yield (68.8 grams) having a melting point of 210°-215° C. and analyzing 78.8 area percent hexabromodiphenoxyethane (2 isomers) with lesser amounts of dibromo (2.4 area percent), tetrabromo (4.4 area percent) and heptabromodiphenoxyethanes (9.4 area percent).

EXAMPLE 2

The procedure of Example 1 was repeated but using a cook period of only 9 hours at ambient temperature. Product was obtained in 99% yield (68.7 grams) having a melt point of 215°-221° C. and analyzing 94.9 area percent hexabromodiphenoxyethane (2 isomers), 0.2 area percent dibromo, 1.0 area percent tetrabromo and 2.7 area percent heptabromodiphenoxyethane.

EXAMPLE 3

The process of Example 1 was repeated except using only a 6 hour cook period at ambient temperature. Product was obtained in 97.4% yield (67.0 grams) having a melt point of 211°-216° C. and analyzing by gas chromatograph 94.7 area percent hexabromodiphenoxyethane (2 isomers), 0.3 area percent dibromo, 2.0 area percent tetrabromo and 2.2 area percent heptabromodiphenoxyethanes.

EXAMPLE 4

This example is the same as Example 1 except only 191.8 grams (1.2 moles) of bromine was used and the initial cook period was 2.5 hours at 45° C. The reaction mixture was then further diluted with 20 mls of 1,2-dichloroethane and cooked for an additional 5 hours at 45° C. Yield was 97.1% (66.8 grams) of a product having a melt point of 207°-217° C. and analyzing by gas chromatograph, 93.3 area percent hexabromo-1,2-diphenoxyethane (2 isomers) and 0.2 area percent dibromo, 5.2 area percent tetrabromo and 0.8 area percent heptabromodiphenoxyethanes.

EXAMPLE 5

This example is the same as Example 4 except using methylene chloride as the solvent. The yield was 95.6% (65.8 grams) of product having a melt point of 208°-211° C. and analyzing by gas chromatograph 94.5 area percent hexabromo-1,2-diphenoxyethanes (2 isomers) and 1.2 area percent tetra and 3.5 area percent heptabromodiphenoxyethanes.

EXAMPLE 6

In a reaction vessel was placed 191.8 grams (1.2 moles) of bromine. To this was added a solution of 21.4 grams (0.1 moles) of 1,2-diphenoxyethane in 40 mls of methylene chloride at 20°-25° C. over a 30 minute period. The mixture was then heated to reflux (about 46° C.) and held at reflux for 2 hours. It was then further diluted with 20 mls of methylene chloride and refluxed for an additional 6 hour period. Product was recovered as in the previous examples except that a small amount of aqueous NaOH was added after distilling out bromine and solvent to decompose any residual bromine in the aqueous slurry. The filtered product was water washed and dried yielding 66.3 grams (96.4% yield) of a product having a melt point of 212°-218° C. and analyzing 95.2 area percent hexabromo-1,2-diphenoxyethane (2 isomers) and 0.5 area percent dibromo, 2.6 area percent tetrabromo and 0.6 area percent heptabromodiphenoxyethanes.

EXAMPLE 7

This reaction was conducted in the same manner as Example 6 except the amounts were scaled up eight times and the initial and final cook periods at reflux were 2.5 and 5.5 hours. Product was obtained in 97.8% yield (538 grams) having a melt point of 213°-220° C. and analyzing 98.6 area percent hexabromo1,2-diphenoxyethanes and only 0.5 area percent tetrabromo and 1.0 area percent heptabromodiphenoxyethanes.

The other diaryloxyalkanes can be substituted in the above examples on an equal mole basis to give similar results.

The products are useful as fire retardants in a broad range of organic polymers such as polystyrene, rubber-modified polystyrene, polyester, polycarbonates, polyaryl ethers, polyamides, polyimides, polyethylene, polypropylene, SBR rubber and the like. In this use the additives comprise about 5-15 weight percent of the polymer composition.

What is claimed is:

1. A process for brominating a diaryloxyalkane to produce a product containing an average of about 5-7 bromine atoms per molecule, said process comprising;
   (a) commingling a solution of said diaryloxyalkane in a haloalkane solvent with an excess of liquid bromine in the absence of a bromination catalyst at a temperature from about 0° C. up to the reflux temperature of the mixture;
   (b) allowing the resultant mixture to react to form the desired brominated diaryloxyalkane; and
   (c) recovering said brominated diaryloxyalkane.

2. A process of claim 1 wherein said diaryloxyalkane is 1,2-diphenoxyethane.

3. A process of claim 2 using at least 12 moles of bromine per mole of 1,2-diphenoxyethane to produce a product containing an average of about 5-7 bromine atoms per molecule.

4. A process of claim 2 wherein said haloalkane solvent is methylene chloride.

5. A process of claim 4 using at least 12 moles of bromine per mole of 1,2diphenoxyethane to produce a product containing an average of about 5-7 bromine atoms per molecule.

6. A process of claim 1 wherein said solution of diaryloxyalkane is added to said bromine.

7. A process of claim 6 wherein said diaryloxyalkane is 1,2-diphenoxyethane.

8. A process of claim 7 using at least 12 moles of bromine per mole of 1,2-diphenoxyethane to produce a product containing an average of about 5-7 bromine atoms per molecule.

9. A process of claim 8 wherein said haloalkane solvent is a chloroalkane.

10. A process of claim 9 wherein said chloroalkane is methylene chloride.

11. A process of claim 6 using at least 12 moles of bromine per mole of diaryloxyalkane.

12. A process of claim 11 wherein said solvent is methylene chloride.

13. A process of claim 12 wherein said diaryloxyalkane is 1,2-diphenoxyethane and the addition of said solution is started at a temperature from ambient up to about 35° C.

14. A process of claim 13 wherein the reaction mixture is heated to up to about reflux to complete the bromination reaction.

15. A process for making brominated diphenoxyethane consisting predominantly of hexabromodiphenoxyethane and containing only minor amounts, less than 5 weight percent each, of tetrabromodiphenoxyethane and heptabromodiphenoxyethane, said process comprising commingling a haloalkane solution of 1,2-diphenoxyethane with liquid bromine at a temperature from about 0° C. up to the reflux temperature of the mixture in the substantial absence of a halogenation catalyst, the amount of said bromine being at least 12 moles per mole of said 1,2-diphenoxyethane.

16. A process of claim 15 wherein said haloalkane is methylene chloride.

17. A process of claim 16 wherein said solution is added to said liquid bromine.

18. A process of claim 17 wherein at least about 18 moles of bromine are used per mole of said diphenoxyethane.

19. A process of claim 18 conducted at a temperature from ambient up to reflux.

* * * * *

UNITED STATES PATENT AND TRADEMARK OFFICE
CERTIFICATE OF CORRECTION

PATENT NO. : 4,716,251
DATED     : December 29, 1987
INVENTOR(S) : Gerald L. Scymanski, Et Al.

It is certified that error appears in the above-identified patent and that said Letters Patent is hereby corrected as shown below:

Column 1, line 18, reads "Bzaokenridge" and should read
-- Brackenridge --.

Column 1, line 55, reads "1,(2,4-dibromophenoxy)" and should
read -- 1-(2,4-dibromophenoxy) --.

Column 4, line 28, reads "hexabromol,2-" and should read
-- hexabromo-1,2- --.

Column 4, line 62, reads "1,2diphenoxyethane" and should
read -- 1,2-diphenoxyethane --.

Signed and Sealed this

Thirty-first Day of May, 1988

Attest:

DONALD J. QUIGG

Attesting Officer        Commissioner of Patents and Trademarks